(12) United States Patent  
Smith

(10) Patent No.: US 11,439,553 B2  
(45) Date of Patent: Sep. 13, 2022

(54) MULTIMODAL DEVICE FOR TRANSDERMAL TREATMENTS

(71) Applicant: André Hugo Smith, Central (HK)

(72) Inventor: André Hugo Smith, Central (HK)

( * ) Notice: Subject to any disclaimer, the term of this patent is extended or adjusted under 35 U.S.C. 154(b) by 82 days.

(21) Appl. No.: 15/974,901

(22) Filed: May 9, 2018

(65) Prior Publication Data

US 2019/0343702 A1  Nov. 14, 2019

(51) Int. Cl.  
*A61M 16/22* (2006.01)  
*A61G 10/02* (2006.01)  
*A61K 38/19* (2006.01)  
*A61M 16/10* (2006.01)

(52) U.S. Cl.  
CPC ........... *A61G 10/026* (2013.01); *A61M 16/22* (2013.01); *A61G 2203/20* (2013.01); *A61K 38/195* (2013.01); *A61M 16/101* (2014.02); *A61M 2016/1025* (2013.01); *A61M 2202/0208* (2013.01); *A61M 2205/3368* (2013.01)

(58) Field of Classification Search  
CPC . A61G 10/026; A61G 2203/20; A61M 16/22; A61M 16/101; A61M 2202/0208; A61M 2016/1025; A61M 2205/3368; A61M 21/02; A61M 2202/0225; A61M 2021/0044; A61M 2021/0055; A61M 2021/0066; A61M 16/16; A61M 2205/587; A61M 2205/054; A61M 2205/057; A61M 2205/052; A61K 38/195; A61H 33/14  
See application file for complete search history.

(56) References Cited

U.S. PATENT DOCUMENTS

| | | | |
|---|---|---|---|
| 6,243,609 B1 * | 6/2001 | Lee | A61H 39/06 607/100 |
| 6,652,479 B2 | 11/2003 | Rasor et al. | |
| 7,875,173 B1 * | 1/2011 | Barnes | A61H 33/14 210/167.1 |
| 8,440,617 B2 | 5/2013 | Velazquez et al. | |

(Continued)

FOREIGN PATENT DOCUMENTS

| | | |
|---|---|---|
| WO | 2002011661 A2 | 2/2002 |
| WO | 2008032257 | 3/2008 |

(Continued)

OTHER PUBLICATIONS

OZONE Therapy, https://web.archive.org/web/20161012215650/https://www.illusionshair.co.za/ozonetherapylivinesante.html, retrieved Apr. 2, 2019, published on Oct. 12, 2016 as per wayback machine.

(Continued)

*Primary Examiner* — Scott M. Getzow  
(74) *Attorney, Agent, or Firm* — Edwin S. Flores; Daniel J. Chalker; Chalker Flores, LLP

(57) ABSTRACT

The present invention includes an apparatus for transdermal treatments comprising: an openable enclosure for a subject in communication with three or more sources of treatment modalities selected from: a source of ozone; a source of steam, a source of $CO_2$/Carbonic Acid; a source of Far Infrared; and a source of pulsed electromagnetic fields (PEMF), wherein each of the three or more sources is in communication with an interior of the openable enclosure to treat the subject transdermally.

32 Claims, 9 Drawing Sheets

(56) References Cited

U.S. PATENT DOCUMENTS

| | | | |
|---|---|---|---|
| 8,517,909 | B2 | 8/2013 | Honeycutt et al. |
| 9,592,171 | B2 | 3/2017 | Delp, II et al. |
| 9,713,328 | B2 | 7/2017 | Lima |
| 9,937,150 | B2 | 4/2018 | Wang et al. |
| 2009/0314217 | A1* | 12/2009 | Hurwitz ............... A61H 33/066 119/400 |
| 2010/0305497 | A1 | 12/2010 | Tanaka et al. |
| 2012/0065576 | A1* | 3/2012 | Stryker ................ A61M 35/30 604/20 |
| 2016/0256638 | A1* | 9/2016 | Sarangapani ......... A61M 35/00 |
| 2017/0173295 | A1* | 6/2017 | Sanderson ............. A61B 5/024 |
| 2018/0043174 | A1* | 2/2018 | Gurfein ................. A61N 2/004 |

FOREIGN PATENT DOCUMENTS

| | | |
|---|---|---|
| WO | 2008146250 A1 | 12/2008 |
| WO | 2016113325 A1 | 7/2016 |

OTHER PUBLICATIONS

Berg, H., et al., "Bioelectromagnetic Field Effects on Cancer Cells and Mice Tumors," Electromagnetic Biology and Medicine, Nov. 9, 2010, vol. 29, pp. 132-143.

Borrelli, E., et al., "Visual Improvement Following Ozonetherapy in Dry Age Related Macular Degeneration; a Review," Medical Hypothesis, Discovery & Innovation, Opthalmology Journal, 2013, vol. 2:2, pp. 47-51.

Cossarizza, D. Monti, et al., "Extremely Low Frequency Pulsed Electromagnetic Fields Increase Cell Proliferation in Lymphocytes from Young and Aged Subjects," Biochemical and Biophysical Research Communications, vol. 160, No. 2, Apr. 28, 1989, pp. 692-698.

Faisal, W., et al., "Not All Body Surface Area Formulas are the Same, but Does it Matter?" to the Editor, Journal of Global Oncology, vol. 2, Iss 6, Dec. 2016, pp. 436-437.

Kucuksezer, U., et al., "A stimulatory role of ozone exposure on human natural killer cells," Immunol. Invest., 2014, 43(1), pp. 1-12.

Tomiyama, C., et al., "The effect of repetitive mild hyperthermia on body temperature, the autonomic nervous system, and innate and adaptive immunity," Biomedical Research (Tokyo) 36:2, Jan. 2015, pp. 135-142.

Zychowska, M., et al., "Effects of sauna bathing on stress-related genes expression in athletes and non-athletes," Anals of Agricultural and Environmental Medicine, Feb. 2017, vol. 24, No. 1, pp. 104-107.

* cited by examiner

MULTIMODAL DEVICE FOR TRANSDERMAL TREATMENTS

CROSS-REFERENCE TO RELATED APPLICATIONS

None.

STATEMENT OF FEDERALLY FUNDED RESEARCH

None.

TECHNICAL FIELD OF THE INVENTION

The present invention relates in general to the field of devices and methods for treatment using multiple transdermal treatment modalities.

BACKGROUND OF THE INVENTION

Without limiting the scope of the invention, its background is described in connection with transdermal treatments.

One such device and method is taught in U.S. Pat. No. 9,937,150, issued to Wang, et al., entitled "Method for enhancing the oxygenation level of tissue cells as an alternative method for hyperbaric oxygen therapy." Briefly, these inventors are said to teach a method for substituting for or acting with the hyperbaric oxygen therapy to improve hypoxia by administrating a phthalide compound that increases the oxygen release efficiency of blood hemoglobin (Hb) in the subject and further increase the cellular oxygenation level, and when the phthalide compound substitutes for or act with the hyperbaric oxygen therapy, the common adverse side effects of the hyperbaric oxygen therapy, such as barotrauma, decompression sickness and oxygen poisoning, are prevented.

Another such device is taught in U.S. Pat. No. 9,713,328, issued to Verri Lima, entitled "Hyperbaric criogenesis chambers." Briefly, this inventor is said to teach a hyperbaric cryogenesis chamber equipped for medical usage, extracorporeal, and capable of promoting the proliferation and preservation of cells. They hyperbaric cryogenesis chamber includes compartments with containers that host tissues or cells in solution with nutrients, that bear pressures higher and lower to sea level and a cold system inside that lowers the environmental temperature and maintains it permanently.

Yet another device is taught in U.S. Pat. No. 9,592,171, issued to Delp, II, et al., entitled "Hyperbaric chamber system and related methods." Briefly, these inventors are said to teach a hyperbaric chamber control system and apparatus for controlling, measuring, and reporting hyperbaric chamber sessions using the partial pressure of oxygen as the lead variable. Air is gently flushed from the bottom of the chamber, upwards, and a nostril-level oxygen pickup measures oxygen concentration in the chamber, wherein the chamber pressure and oxygen concentration values are used to calculate the partial pressure of oxygen, and the session time is adjusted so that a subject treatment accurately reflects prescribed treatment.

One method of treatment is taught in U.S. Pat. No. 8,440,617, issued to Velazquez, et al., entitled "Hyperbaric treatment in wound healing." Briefly, these inventors are said to teach methods for treating chronic dermal ulcers using hyperbaric treatment in combination with progenitor cells and chemokine homing factors. Specifically, the hyperbaric treatment is used to treat chronic wounds resulting from diabetes mellitus using compositions comprising EPC and SDF-1A under hyperbaric condition that accelerate wound healing.

However, despite these advancements, a need remains for improved transdermal treatment modalities that maximize the treatment of the subject and minimizes the time of treatment.

SUMMARY OF THE INVENTION

In one embodiment, the present invention includes an apparatus for transdermal treatments comprising: an enclosure for a subject in communication with three or more sources of treatment modalities selected from: a source of steam; a source of ozone; a source of $CO_2$/Carbonic Acid; a source of Far Infrared; and a source of pulsed electromagnetic fields (PEMF), wherein each of the three or more sources is in communication with an interior of the enclosure to treat the subject transdermally. In one aspect, apparatus further comprises one or more additional treatments selected from: a source for pure oxygen; one or more photon color lights; a source for an essential oil infusion for aromatherapy; and a source of frequency specific microcurrents. In another aspect, the enclosure is a whole body enclosure with an opening for a head of a user. In another aspect, the PEMF comprises a plurality of coils sufficient to provide treatment to at least a portion of a body of the subject, or a whole body of the subject, concurrently. In another aspect, the apparatus further comprises one or more processors connected to the three or more sources of treatment modalities, wherein the processor controls one or more valves that open or close the introduction of treatment modalities into the enclosure, or wherein the source of PEMF is controlled separately. In another aspect, the ozone is further defined as comprising at least one of: ozone sauna or topical cupping. In another aspect, the subject is a human. In another aspect, the enclosure is adapted to include an exercise equipment. In another aspect, the apparatus further comprises further comprising at least one of: an ozone vaginal insufflation probe, a second ozone generator, an auxiliary ozone feed for vaginal insufflation/cupping simultaneously with or without sauna, or an ozone water drinking source. In another aspect, the apparatus further comprises one or more specific, programmable frequency specific microcurrents. In another aspect, the three or more sources of treatment modalities are provided concurrently, in series, overlapping, continuously, pulsatile, or combinations thereof. In another aspect, the three or more sources of treatment modalities are programmed into a processor to optimize treatment of the subject. In another aspect, a complete treatment of the subject can be provided in half the time of a treatment in an ozone/heat device. In another aspect, the apparatus further comprises a heart rate monitor that at least one of: tracks heart rate, turns off the apparatus when a certain combination of heart rate and time is reached, or provides an emergency shutdown. In another aspect, the apparatus further comprises an ozone degradator that degrades the ozone into $O_2$ prior to exiting the enclosure. In another aspect, the enclosure comprises two overlapping PEMF fields formed within the enclosure to provide the subject with at least partially amplified magnetic fields. In another aspect, the apparatus can include 4, 5, 6, 7, or eight modalities in communication with the enclosure.

In another embodiment, the present invention includes a method of treating a subject transdermally comprising:

providing an enclosure for a subject in communication with three or more sources of treatment modalities selected from: a source of steam; a source of ozone; a source of $CO_2$/Carbonic Acid; a source of Far Infrared; and a source of pulsed electromagnetic fields (PEMF), wherein each of the three or more sources is in communication with an interior of the enclosure to treat the subject transdermally. In one aspect, the method further comprises the steps of providing a session to a subject that comprises: a $CO_2$/Carbonic acid treatment for 0-8 Minutes, an ozone cycle of 0-25 minutes, a high intensity PEMF for 0-12 minutes, and a sauna or a far infrared treatment, or both, or an ozone cycle of up to 30 mins if $CO_2$ is set to 0 mins. In one aspect, the method further comprises the steps of providing a session to a subject that comprises: a $CO_2$/Carbonic acid treatment from 3-8 Minutes concurrently with an ozone cycle of 0-25 minutes, and a high intensity PEMF from 0-12 minutes, and a sauna or a far infrared treatment, or both. In one aspect, the method further comprises one or more additional treatments selected from: a source for pure oxygen; one or more photon color lights; a source for an essential oil infusion, a source for aromatherapy; and a source of frequency specific microcurrents. In another aspect, the enclosure is a whole body enclosure with an opening for a head of a user. In another aspect, the PEMF comprises one or more coils sufficient to provide treatment to at least a portion of a body of the subject, or a whole body of the subject, concurrently. In one aspect, the method further comprises one or more processors connected to the three or more sources of treatment modalities, wherein the processor controls one or more valves that open or close the introduction of treatment modalities into the enclosure. In another aspect, the ozone is further defined as comprising at least one of: ozone sauna or topical cupping. In another aspect, the subject is a human. In another aspect, the enclosure is adapted to include an exercise equipment. In another aspect, the method further comprises at least one of an ozone vaginal insufflation probe, an ozonated water drinking source, one or more specific, programmable frequency specific microcurrents. In another aspect, the three or more sources of treatment modalities are provided concurrently, in series, overlapping, continuously, pulsatile, or combinations thereof. In one aspect, the method further comprises a heart rate monitor that at least one of: tracks heart rate, turns off the apparatus when a certain combination of heart rate and time is reached, or provides an emergency shutdown. In one aspect, the method further comprises an ozone degradator that degrades the ozone into $O_2$ prior to exiting the enclosure. In one aspect, the method further comprises identifying a transdermal treatment for the subject that controlling the type of treatment modality and the time to treat the subject. In another aspect, the enclosure comprises two overlapping PEMF fields formed within the enclosure to provide the subject with at least partially amplified magnetic fields. In another aspect, the apparatus can include 4, 5, 6, 7, or eight modalities in communication with the enclosure.

In another embodiment, the present invention includes the use of an apparatus for transdermal treatments treating a subject comprising: an enclosure for a subject in communication with three or more sources of treatment modalities selected from: a source of ozone; a source of $CO_2$/Carbonic Acid; a source of Far Infrared; and a source of pulsed electromagnetic fields (PEMF), wherein each of the three or more sources is in communication with an interior of the enclosure to treat the subject transdermally. In another aspect, the apparatus can include 4, 5, 6, 7, or eight modalities in communication with the enclosure.

In another embodiment, the present invention includes a n apparatus for transdermal treatments comprising: an enclosure that comprises a source of steam for a subject, in communication with two or more sources of treatment modalities selected from: a source of ozone; a source of $CO_2$/Carbonic Acid; a source of Far Infrared; and a source of pulsed electromagnetic fields (PEMF), wherein each of the three or more sources is in communication with an interior of the enclosure to treat the subject transdermally. In another aspect, the apparatus can include 4, 5, 6, 7, or eight modalities in communication with the enclosure.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
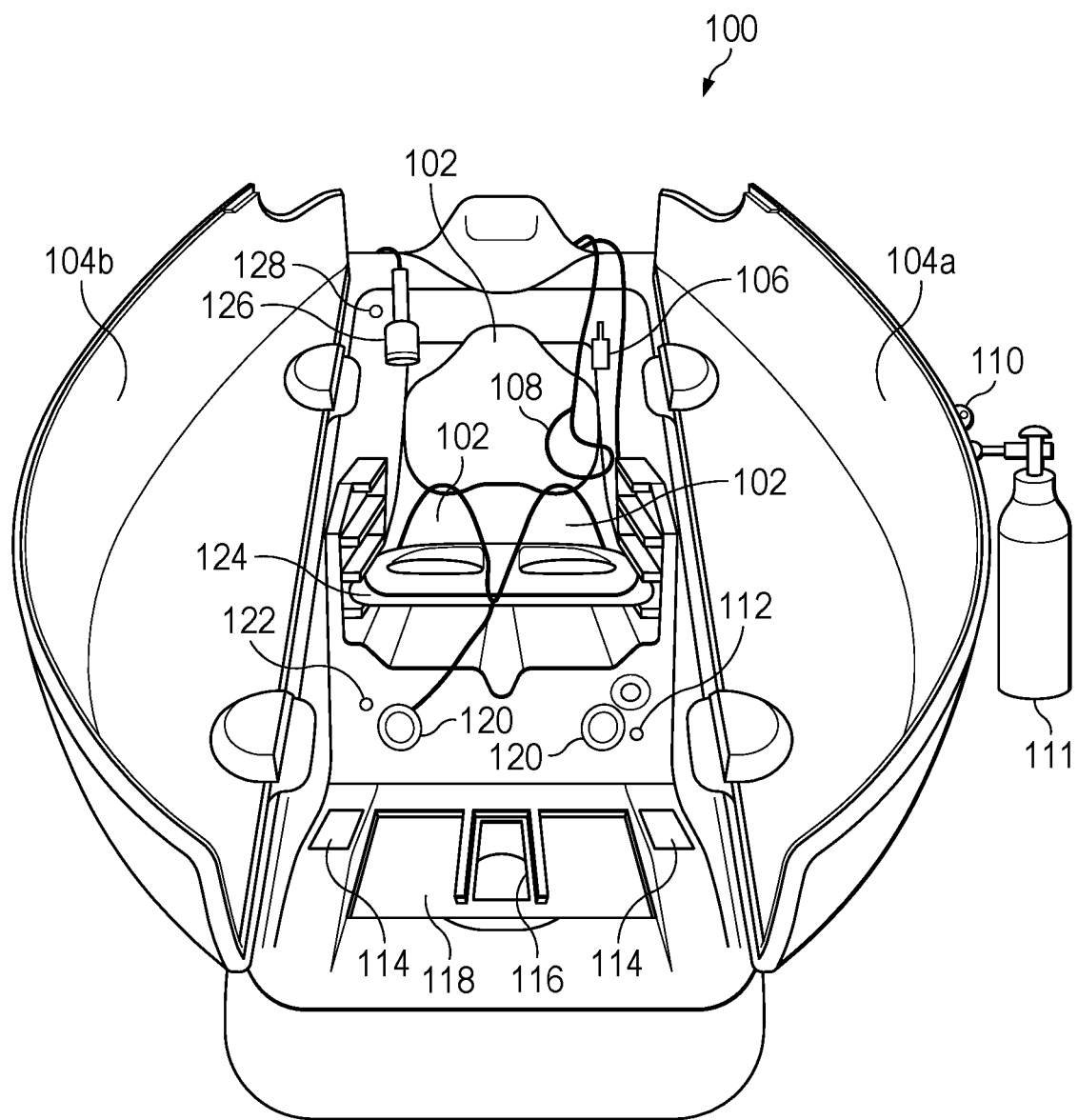
FIGS. 1A and 1B show one embodiment of a multimodal treatment device of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The apparatus of the present invention provides for the first time multiple treatment modalities within a single treatment chamber to maximize transdermal delivery of the various components or modalities while minimizing treatment time. The combination of treatment modalities is used to, at least one of, detoxify the body, improve circulation, boost energy, and strengthen the immune system. Using the present invention, it has been found that the device is at least 7× more efficient that conventional saunas to: (1) detoxify the body, and/or (2) chelate heavy metals by injecting ozonating steam into the chamber or enclosure. Further, the present invention provides to different modalities to chelate and remove toxins and/or heavy metals from the body, including both in-body chelation and elimination of the toxins/heavy metal, but by using a sauna a number of these toxins are removed via sweat.

The present invention also provides a modality that includes a $CO_2$/carbonic acid treatment. The $CO_2$/carbonic acid treatment is typically initiated at start-up or soon thereafter (at 1-5 minutes) after the injection of a steam sauna (with or without ozone), which in certain modalities may also be augmented by far infrared.

The present invention also provides a modality that includes a whole or partial body high-intensity pulsed electro-magnetic field (PEMF). The PEMF can be provided in the form of one or more blankets (or can be embedded directly into the chamber) to provide access and exposure of the entire body of a subject with the PEMF. To do so, one or more PEMF coils are provided that direct PEMF at a portion or the whole body. As with the treatment above, the PEMF modality or treatment can be used during the entire session, during a portion of the session, in a pulsatile manner, with increasing or decreasing intensity, to certain portions of the body, and combinations thereof.

Thus, the present invention when three or more modalities permits, for the first time, for a combination of treatments that can occur concurrently or in series (one at a time), such as hyperthermic ozone, hyperthermic $CO_2$/carbonic acid, hyperthermic sauna, hyperthermic PEMF, ozone, hyperthermic $CO_2$/carbonic acid, hyperthermic sauna, hyperthermic PEMF.

Figure 1B:
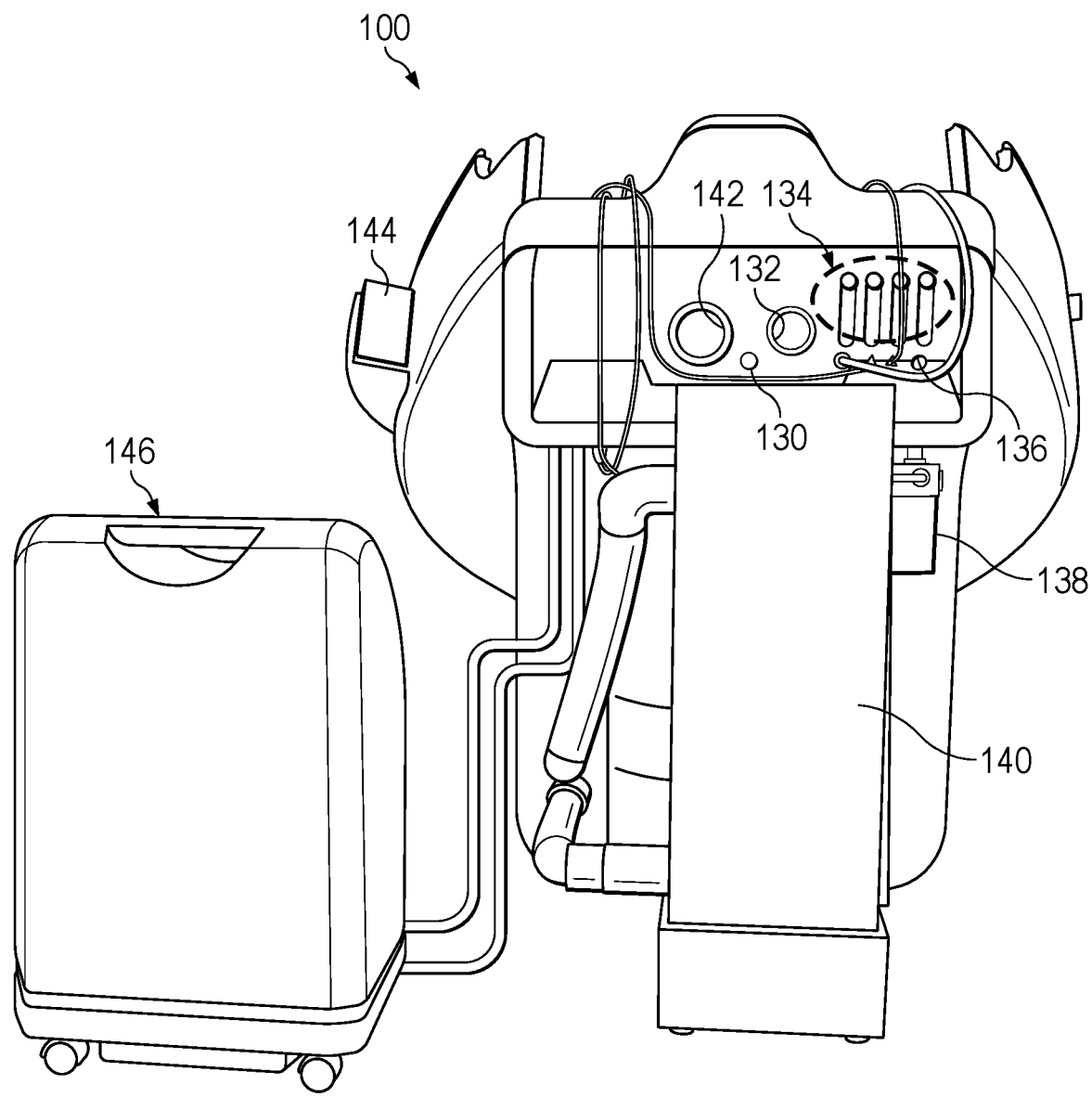

FIGS. 1A and 1B show one embodiment of a multimodal treatment device 100 of the present invention. FIG. 1A shows a front view of the enclosure 102 that includes doors 104a and 104b, which rotate about hinges that form an enclosure for the transdermal treatments of the present invention. The multimodal treatment device 100 and its enclosure 102 provide certain transdermal treatment modalities for a subject, wherein a subject (not depicted) in communication with three or more sources of treatment modalities selected from: a source of steam; a source of ozone; a source of $CO_2$/Carbonic Acid; a source of Far Infrared; and a source of pulsed electromagnetic fields (PEMF), wherein each of the three or more sources is in communication with an interior of the enclosure to treat the subject transdermally. FIG. 1A shows a multimodal treatment device 100 that includes additional features and modalities. For example, FIG. 1 is also shown to include a version that has a heart rate monitor 106, an oxygen breathing apparatus 108, a $CO_2$ tank and regulator 110 and $CO_2$ tank 111, a first ozone inlet 112, electrotherapy foot plates 114, steam source or jet 116, a foot rest 118, a source of colored photon lights 120, a second (auxiliary or optional) ozone source 122, an adjustable seat 124, a ultrasonic cavitation source 126, and a third ozone source 9128 (also optional).

The exact locations of the various sources of different modalities can be varied so long as they are in communication with the interior of the enclosure, and thus, the patient or subject during a treatment. The enclosure can also be varied in size such that, e.g., an exercise equipment (e.g., a stationary bicycle, weights, resistive elements, etc.) can be used by the patient or subject during a treatment. Further-more, control logic is provided such that a user or care provider can pre-program a treatment regimen, such as those disclosed herein, to optimize a specific treatment sequence for a specific condition or conditions. Not depicted in this figure is the addition of PEMF blankets that can be placed below the user and one the user before use or that can be embedded or integral with the enclosure, including the seating portion and the door or doors. Likewise, the photonic treatments can be positioned in just one location as shown, or can be embedded into the enclosure such that the entire body (or portions thereof) can be directly targeted. In this embodiment, steam is shown as the source of heat within the enclosure, however, other radiative sources of heat can also be used within the enclosure. It is also possible to provide a source for cooling, that is, to reduce overall body temperature or simply to reduce body temperature during a cooling down phase of a treatment.

FIG. 1B shows a back view or portion of the multimodal treatment device 100, that includes an on/off switch 130, a water gauge 132, flow meters 134, one or more flow dials or controls, such as frequency specific microcurrents (FSM) 136, a humidifier bottle 138, an ozone destructor 140, a water inlet 142, a monitor 144, and an oxygen concentrator 146. Typically, a care provider will monitor the time, intensity, and conditions within the enclosure during a treatment.

Every parameter (duration, temperature, intensity/concentration) is adjustable both before and during the session, to suit the needs of the patient or subject, either manually or automatically/programmably. It is also possible to set safeguards, such as minimum and/or maximum ranges for treatment that are preprogrammed into a control processor connected to valves that control the inflow of the various treatment modalities. For example, the heart rate monitor includes an option to set a limit, such that if the limit is surpassed the entire machine shuts-down. This is an added safety mechanism for those with cardiovascular concerns.

Typically, the shell/chamber of the enclosure can be made from, e.g., fiberglass with a coating (e.g., an Acrylonitrile butadiene styrene (ABS) or other coating). The materials from which the enclosure is made and/or any coatings are selected such that is non-reactive with the ozone, heat, steam, $CO_2$ or other gasses or other modalities of treatment.

In the embodiment shown in FIG. 1A, dual ozone generators as depicted, for examples, one generator can be dedicated to filling the chamber with ozone (i.e. the Ozone Sauna; 1× generator for optional Ozone vaginal insufflation/cupping (allows for simultaneous application of Ozone cupping/vaginal insufflation without interfering with the Ozone Sauna; and allows for using the cupping/insufflation as a stand-alone modality i.e. can also be used without starting a sauna session), while another can be used for specific treatments to specific regions, such as vaginal insufflation or directed treatment of one or more regions or orifices. The enclosure can be adapted for the user to be sitting, kneeling, standing, or using some type of equipment within the enclosure. Further, the enclosure can also be modified to accommodate non-human animals, such as domestic animals or pets (cats, dogs, rabbits, pigs), horses, cows, or other large animals.

In order to prevent leakage of ozone outside the treatment enclosure, this embodiment includes a small built-in ozone destructor for during-session ozone destruction. It is also possible, but not always preferred, to vent the ozone to the outside environment. A large, external high-volume ozone destructor can also be used for removing and destructing the entire volume of ozone from the chamber after the session and before opening the chamber doors (so as not to expose the room to ozone). The present invention can also includes an oxygen concentrator to feed the ozone generators and provide humidified oxygen for the pure oxygen breathing modality.

The present invention different from other devices in a number of ways. First, there is a difference in how the modalities are normally applied to a patient or subject, including (1) Ozone therapy: the most common method of application is intravenous (minor and major autohemotherapy); or rectal insufflation; (2) $CO_2$/carboxy therapy: is used aesthetically by injection; or in balneotherapy ($CO_2$ baths); (3) Whole body hyperthermia: dry (infrared) or wet (steam) saunas; (4) Microcurrent: electrodes for hands and/or feet; (5) PEMF: low intensity with mats, and high intensity with loops to target specific areas; (6) Essential oils: inhaled or massaged into skin; and/or (6) Color therapy: practitioner dependent, can be colors only (visual) or colored lights (transdermal and/or visual).

In the limited devices of the prior art, when using these individual modalities, these take a lot of time. In a typical treatment regimen of the prior art, and intravenous ozone treatment can take anywhere from 15 minutes to 3 hours depending on the specific method and equipment, CO2 baths are usually 15-20 minutes, Whole body hyperthermia therapy can take anything from 2-4 hours, Far infrared sauna sessions range between 30 minutes-1 hour, Frequency Specific Microcurrent sessions can be anything from 20 minutes-2 or more hours (depending on the number of frequencies in a program), Low intensity PEMF sessions can range between 30-90 minutes, and conventional high intensity PEMF systems will target only an area of the body at one time (not the majority body, as is achieved with the Hocatt Platinum), with the total time not exceeding 12-15 minutes, Colour light therapy duration is not strictly regulated and depends on the administrator, can be 10 minutes to several hours, and Transdermal essential oils are typically applied with a massage which are typically 30-90 minutes in duration.

The present invention overcomes the time limitations of the prior art devices by providing equivalent or superior treatments by using multiple powerful, non-invasive modalities simultaneously. When placing the body in hyperthermia, it is an ideal condition during which to apply other modalities. By combining these multiple modalities into one device, the present invention has been used to provide 20-30 minute session (thus saving hours of time) while achieving while achieving at least equivalent or greater results.

Other devices that have combined some of these modalities have at the most a maximum of 3 modalities that can be applied simultaneously, for example, there are some devices that combine ozone and sauna (either dry with far infrared, or wet with steam, or both steam and far infrared). Most of them, however, only combine ozone and steam (ozone sauna).

These regular ozone sauna sessions also range in 20-30 minutes in duration, however the addition of the $CO_2$ alone puts the HOCATT™ Platinum miles ahead of conventional ozone saunas. When using all the modalities of the present invention simultaneously the effects are astounding.

The modalities when applied simultaneously potentiate one another. The present invention saves time of the wellness professional and the client. The present invention is non-invasive, no needles, no penetrating the skin. Everything is transdermal, aside from the vaginal insufflation, which is completely optional.

The present invention integrates multiple modalities. The physiologic effects of the multimodal treatment on subjects were determined for different parameters. Typically, the effects are measured for many of parameters over 24-48 range time intervals. Briefly, the subject is placed in the enclosure and the subject treated with one, two, three or more of the modalities for a period of up to 60 minutes. The typical treatment, however, can be reduced with the present invention to as short at 8 minutes, 10, 12, 15, 18, 20, 25, 30, 35, 40, 45, 50, 55 or 60 minutes. After the treatment, blood was drawn every 15-30 minutes, as shown in the graphs. Thus, the "Pre" is just before the multimodal treatment session, "T0" is just after the multimodal treatment session, "T30" is 30 minutes after the session, T60-60 minutes, 90 minutes, 120 minutes, 150 minutes and 180 minutes.

Figure 2:
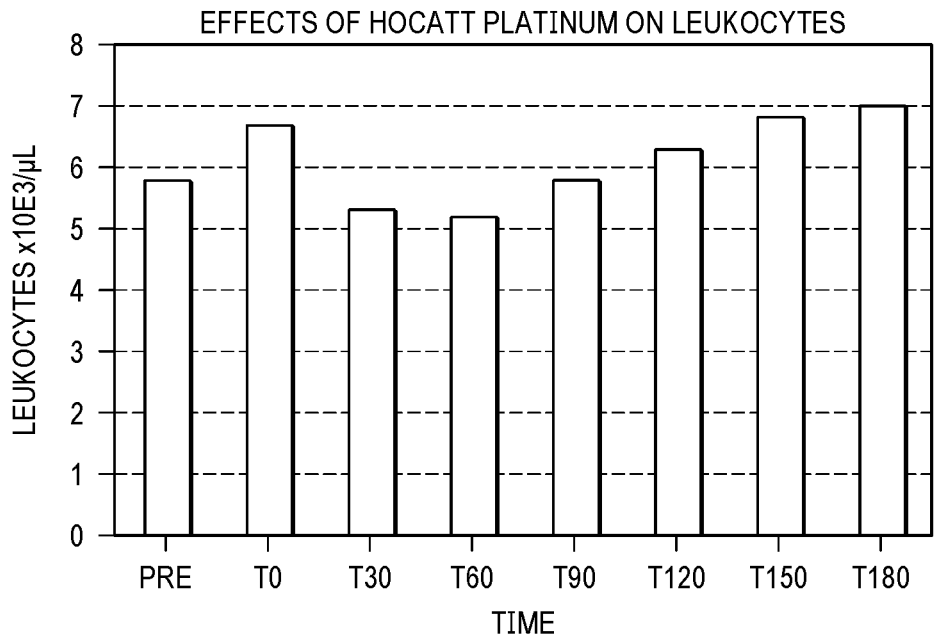
FIG. 2 is a graph that shows the effect of multimodal treatment on leukocytes.
Figure 3:
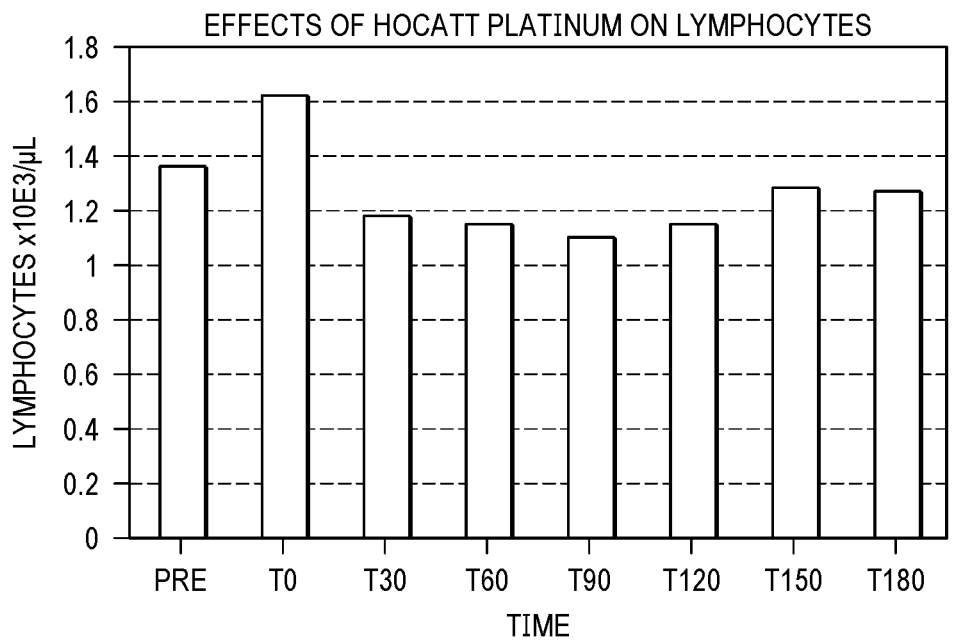
FIG. 3 is a graph that shows the effect of multimodal treatment on lymphocytes.
Figure 4:
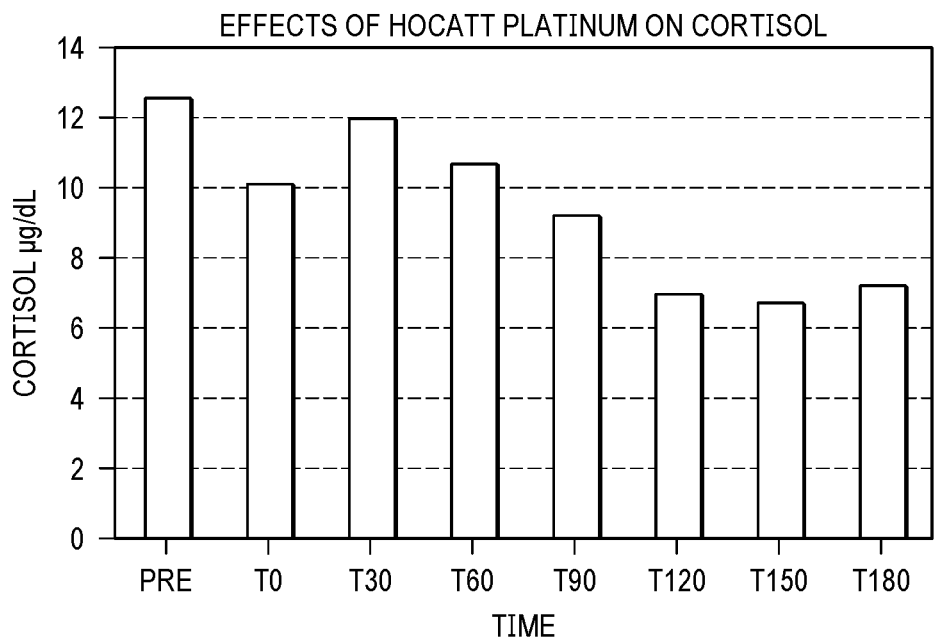
FIG. 4 is a graph that shows the effect of multimodal treatment on cortisol.
Figure 5:
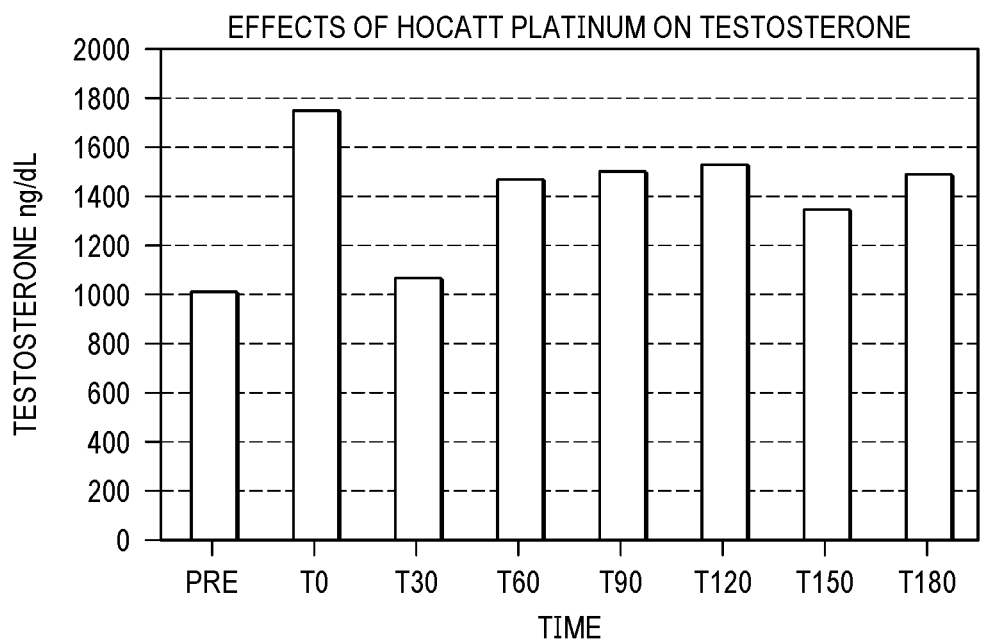
FIG. 5 is a graph that shows the effect of multimodal treatment on testosterone.
Figure 6:
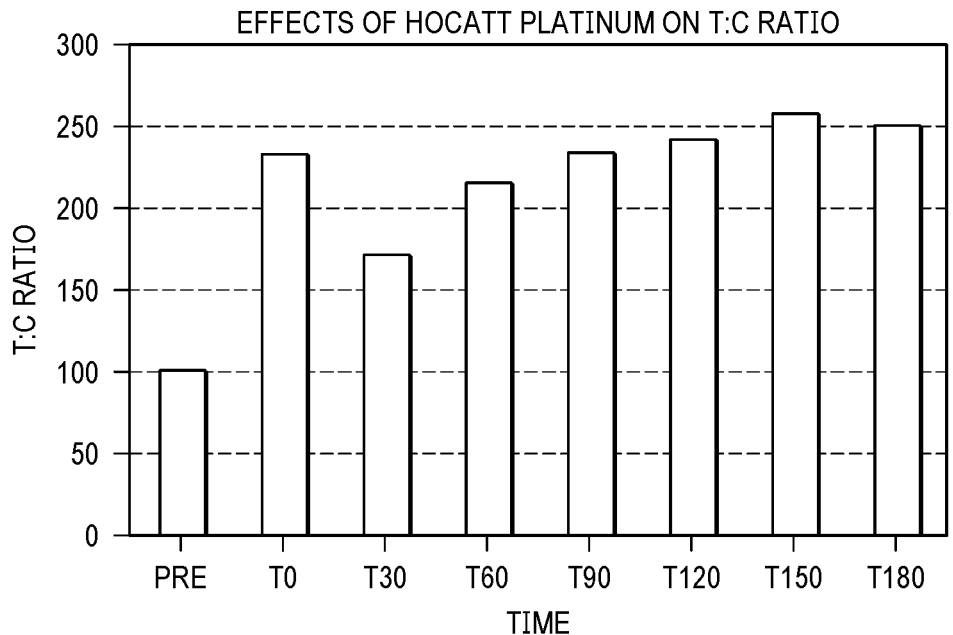
FIG. 6 is a graph that shows the effect of multimodal treatment on a Testosterone:Cortisol (T:C) ratio.
Figure 7:
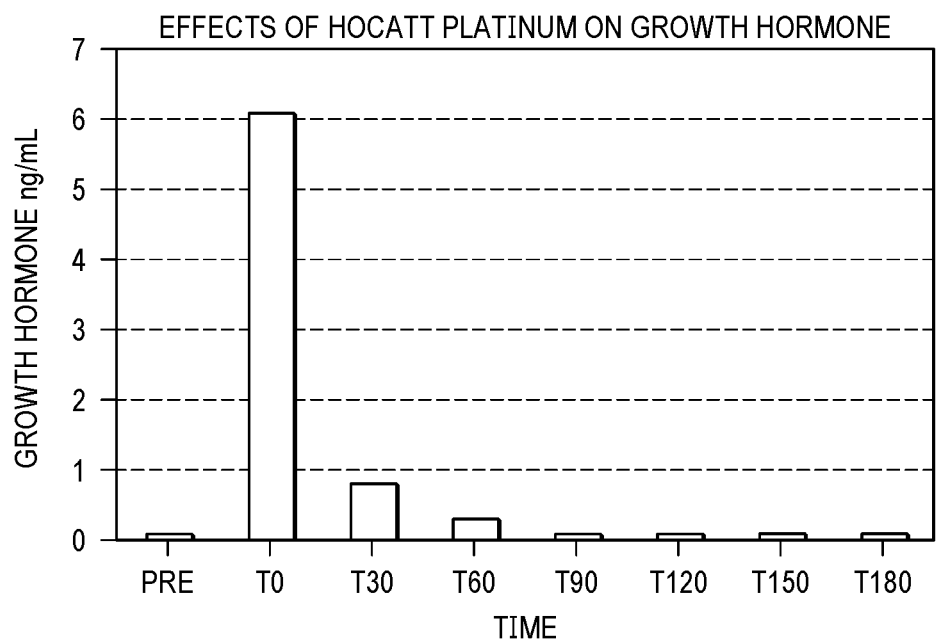
FIG. 7 is a graph that shows the effect of multimodal treatment on growth hormone.

FIG. 2 is a graph that shows the effect of multimodal treatment on leukocytes. FIG. 3 is a graph that shows the effect of multimodal treatment on lymphocytes. FIG. 4 is a graph that shows the effect of multimodal treatment on cortisol. FIG. 5 is a graph that shows the effect of multimodal treatment on testosterone. FIG. 6 is a graph that shows the effect of multimodal treatment a Testosterone:Cortisol (T:C) ratio. FIG. 7 is a graph that shows the effect of multimodal treatment on growth hormone.

The Pulsed Electro-Magnetic Fields (PEMFs) for use with the present invention use magnetic fields to repair and energize the body. PEMFs differ from other electrotherapies in that it is non-contact, in other words there are no electrodes/pads making direct contact with the body. It is not to be confused with micro-current devices. PEMFs induce electrical changes within and around cells, which influences the cell behavior. This results in improved circulation and oxygenation, better transport of nutrients and more energy. PEMFs accelerate the healing process by stimulating the body to repair damaged tissue, while significantly reducing pain. PEMFs also induce reflexology and acupuncture-like actions in the body.

By using a pair of partial and/or whole body PEMF mats within the enclosure, it is possible to create an amplified, controllable PEMF within the enclosure at the same time as other treatment modalities, thus enhancing their activity. The present invention uses a 'sandwich' design for full-body PEMF sessions, in which the double layer amplifies the electromagnetic field, which makes it twice as powerful as regular full-body PEMF devices.

The present invention can be used with various sets of accessories (mats/coils/combo) simultaneously, which allows four (4) application methods. (1) A subject can lie on the bottom mat for a regular full-body PEMF session; (2) A subject can lie in-between the two mats for an amplified full-body 'sandwich' effect; (3) using a long-wire and another accessory can be attached in place of the mats and create a smaller 'sandwich' to target a specific area; or (4) a subject can lie on the bottom mat for a full-body session and attach an accessory in place of the top mat, to use over a specific area, simultaneously.

It was found that present invention reduces time of exposure by increasing the intensity of the field. By contrast, low-intensity PEMFs require sessions up to 90-minutes for effective results. The high-intensity, dual pad, amplified PEMF system of the present invention penetrates deeper into the body, making it more effective in a shorter amount of time, reducing time of treatment to between 1-12 minutes, and in some cases 1-3, 2-6, 4-8, 5-10, and 5-12 minutes for an equivalent treatment using non-amplified PEMFs. Further, the few higher intensity PEMF devices currently available are limited to targeting a specific portion of the body, such as a hand or a limb, that is, one specific area at a time. The problem of dwell time in the device is made more acute when treating a larger build or body mass. Because PEMFs work mainly by imparting energy into the body, the more energy that can be imparted has been found to have the same effect as treatments of 15 or more minutes. Importantly, the amplified PEMF system permits a complete PEMF treatment during the same time as the transdermal treatment, which often cannot exceed 15 minutes. That is, with lower energy PEMF treatments, is it simply not possible to deliver the complete treatment during a concurrent transdermal treatment. In just one 12-minute session, the amplified PEMF system of the present invention has been found to safely deliver a complete body treatment. In certain embodiments, the complete treatment can be delivered in 1, 2, 3, 4, 5, 6, 7, 8, 9, 10, 12, or 15 minutes, when using high intensity PEMF.

The amplified PEMF system of the present invention has been found to provide: (1) beauty and anti-aging, slows aging (via neutralization of free radicals), stimulates collagen synthesis and/or firming of tissues, boosts cellular regeneration and/or repair. (2) Athletic performance the ideal tool for athletes and bio-hackers. PEMFS are legal for competitive sports, and are even been used by Olympic athletes. Enhanced performance includes, increased endurance, boosts energy (maximizes ATP production), optimizes blood and/or tissue oxygenation, relieves anxiety and/or stress, reduces risk of injury, enhanced muscle function, upregulates cellular metabolism, activates RNA and DNA synthesis, stimulates collagen synthesis, faster recovery after exercise, decreases muscle tension, promotes lactic acid excretion, accelerates healing of sore, stiff muscles, reduces pain caused by spasms, accelerates healing of sports injuries, stimulates collagen synthesis, boosts cellular regeneration and/or repair, and reduces swelling and/or inflammation. (3) Cardiovascular System, strengthens blood circulation, normalizes blood pressure, and optimizes blood and/or tissue oxygenation. (4) Pain, significantly reduces pain, relaxes muscles, reduces muscle tension and/or spasms, and relieves migraines and/or tension headaches. (5) Immune System, boosts immune system, improves lymph circulation, enhances cellular detoxification. (6) Energy, increases cellular energy levels, boosts overall energy, floods the body with electrons, energizes electron transport chain, and stimulates ATP production in the mitochondria. (7) Neurological System, helps for insomnia, improves quality of sleep, alleviates stress and/or anxiety, and reduces nervous irritability. (8) Endocrine System, improves osteoporosis, stimulates release of endorphins and promotes well being, normalizes cholesterol levels, improves diabetic neuropathy and vasculopathy (diabetic ulcers). (9) Metabolism, promotes healthy cell metabolism, balances cell-membrane charge, stimulates inter-cellular communication, improves nutrient uptake, promotes higher levels of vitamin a, activates the antioxidant system, destroys free radicals. (10) Healing and/or and/or Regeneration, accelerates injury recovery time, promotes healing of sore, stiff muscles, improves cellular activity and regeneration, enhances tissue repair (stimulates RNA and DNA synthesis), enhances wound healing, reduces fibrous tissue and scars, promotes bone repair and/or regeneration, as well as fracture healing (whether damaged from surgery, injury or disease), enhances joint healing, reduces pain, swelling (edema) and/or inflammation, reduces pain and swelling from sprains, relieves ligament and tendon strain and inflammation, reduces side effects of chemotherapy. (11) Psychiatry, treats mild to severe depression.

Example 1. Pre-Set Programs

It is always best to start the client off on lower settings, and gradually build them up to higher temperatures. In one embodiment, the present invention comes with pre-set programs. Each program has a total of 10 sessions—these sessions have pre-programmed settings where the parameters (such as temperature, ozone concentration, etc.) are gradually increased from session 1 through to session 10. All 10 sessions should be completed in a timely fashion, at 2-3 sessions a week, as these sessions build up the effects and gradually condition the client's body. In the Main Menu, select "Program Options". On the "Program Options" screen, you will see 4 options: Detoxification, Skin, $O_2$ Herbal, and a short-cut to the auxiliary options. Select the desired option, e.g. "Detoxification".

Example 2

The "Detoxification" program is the standard program recommended for new clients. Those with sensitive skin can begin with the "Skin" program, which starts off with much lower temperatures and ozone concentrations. After successfully completing the 10 sessions in the "Skin" program, they can move onto the "Detox" program. The "$O_2$ Herbal" program is for those who want to use have a "regular" sauna session (i.e. without ozone and CO2). This can be an option if both ozone and $CO_2$ is contraindicated.

Example 3

Settings. There can 1, 2, 3, 4, 5, 6, 7, 8, 9, 10 or more pre-set sessions, and the client is advised to complete all 10 sessions for maximum benefit. Once you have selected the session number, you can go ahead and press "start". It is possible to adjust any parameter prior to starting the session, as well as throughout the session (i.e. change the temperature if the client gets too hot/cold).

Example 4

Ozone Screen Settings: Select "$O_3$ screen" to return to the control screen, and set the following parameters for the transdermal Ozone:

Session Time: 20-30 (default) minutes
Temperature: 37 (default)-42° C.
NOTE: high temperatures can cause discomfort and irritability, but it is recommended to increase the heart rate. Always work within your client's comfort levels, and try to gradually build them up to higher temperatures over time.
Steam: 100%
NOTE: the steam should remain at 100%, as it regulates the rate of the temperature increase.
Ozone: 50 (default)-100%
NOTE: it is recommended that you start the client at 50% for both Ozone 1 & 2, and then very gradually increase both percentages as the client gets used to the ozone over several sessions. When using Ozone 2 for auxiliary applications (i.e. cupping), then the Ozone 2 can be increased/decreased per application.

Example 5. Frequency Specific Microcurrents (FSM)

Figure 10:
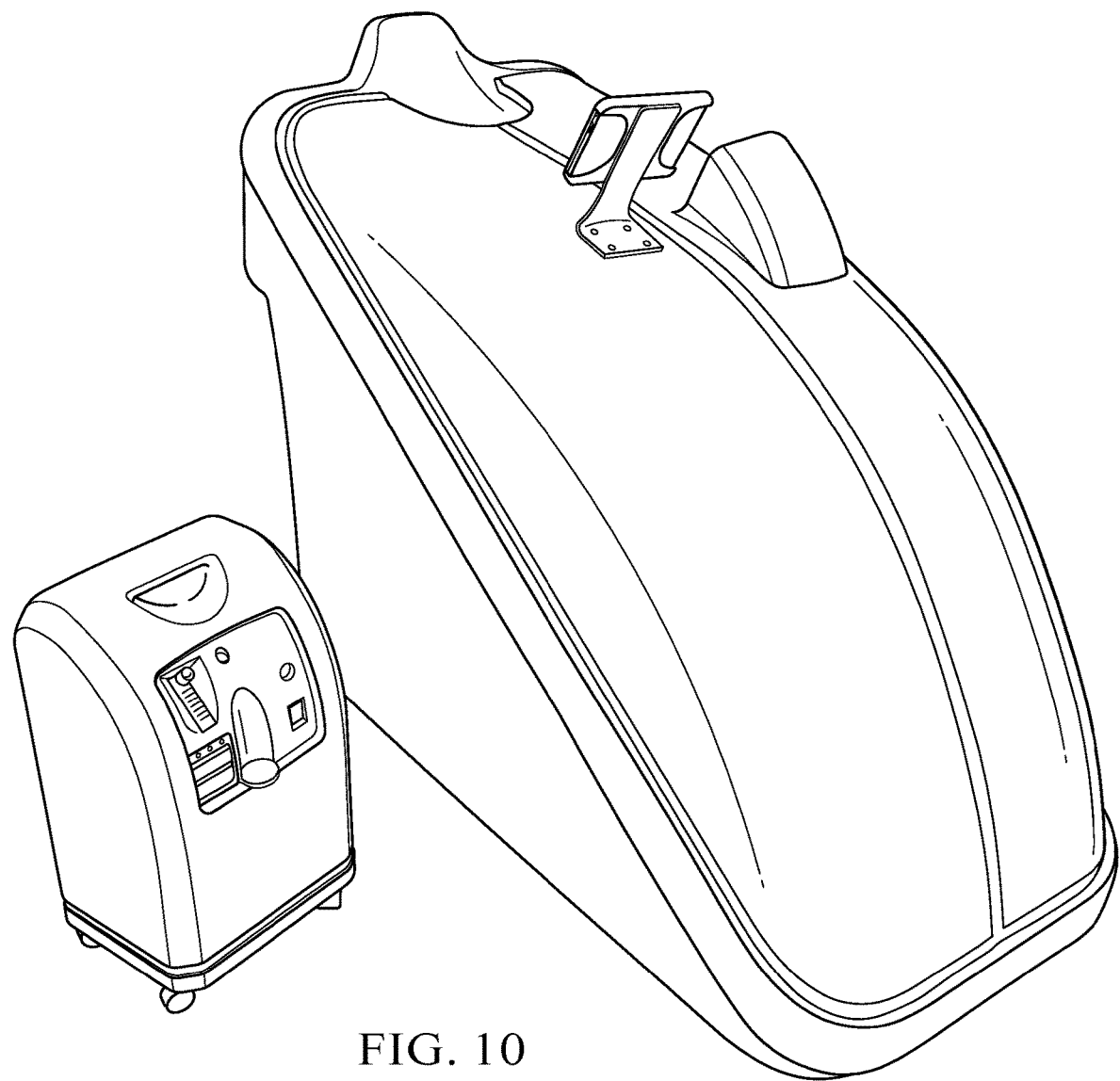
FIG. 10 shows another embodiment of a multimodal treatment device of the present invention.

The FSM program that you choose will cycle through various frequencies at different strengths. You can use the foot-plates or handheld electrodes, or both at the same time. It is typically recommend doing a FSM program during a HOCATT sauna session. However, the FSM can also be administered outside of a sauna session for a longer period of time as a standalone modality. During a sauna session, the cycle time for each frequency is set to 1 minute, i.e. a program with 14 frequencies will take 14 minutes to complete, and a program with 28 frequencies takes 28 minutes, etc. Because the sauna session is 30 minutes long, some FSM programs may finish before the sauna session ends. The client may elect to repeat the program or to do a second FSM program for the remainder of their HOCATT session, which you can then select for them. The basic unit of the present invention, as shown in FIGS. 1A, 1B and 10, incorporates into the enclosure one or more PEMF coils, that is, the one or more coils are built into the enclosure/chamber, so when the PEMF driver is connected to the chamber PEMF is delivered from the back of the enclosure/chamber, but may also be placed on the covers to provide additive PEMF.

Figure 8A:
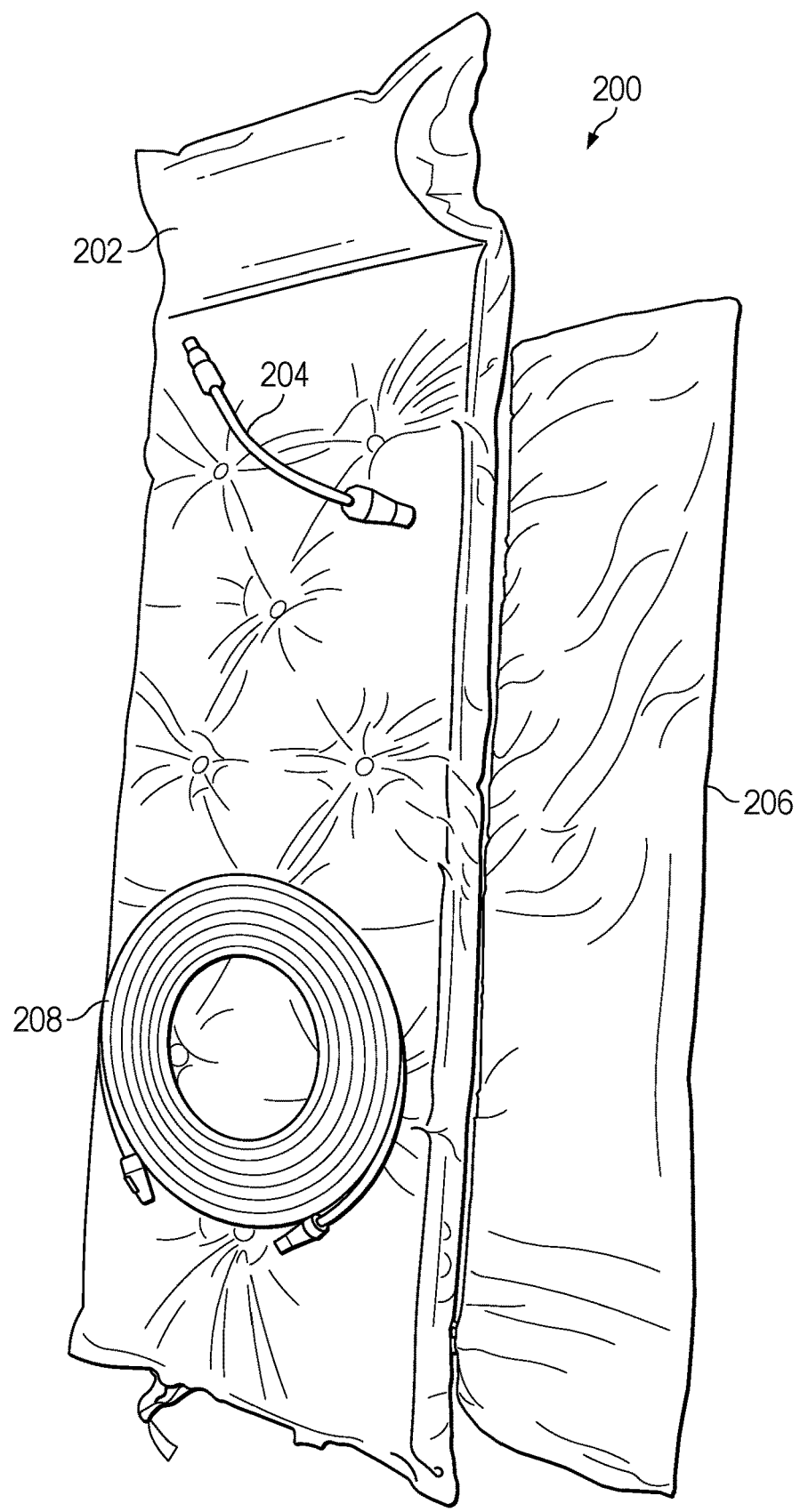
FIGS. 8A and 8B shows one embodiment of a PEMF blanket system for use with the present invention.
Figure 8B:
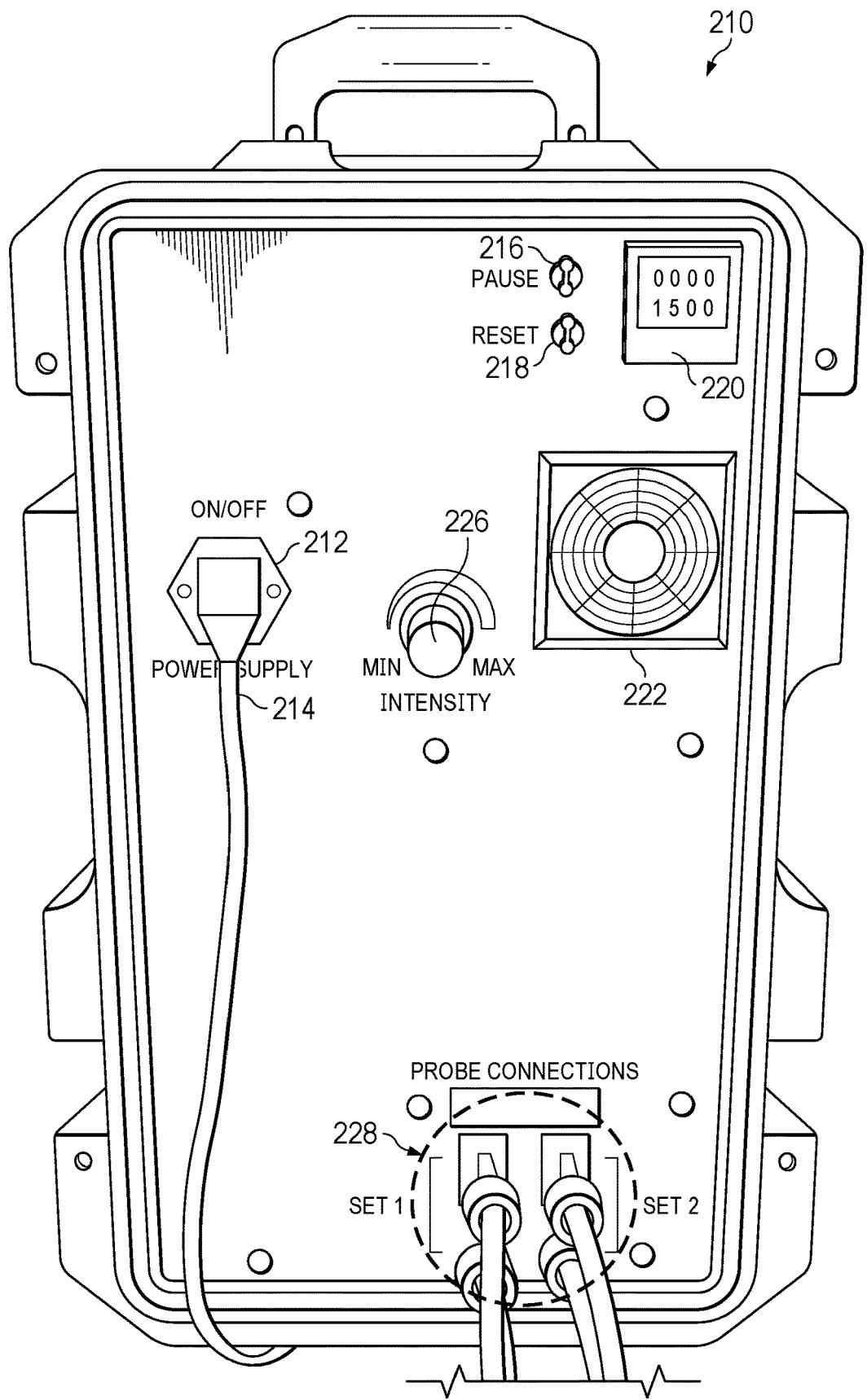

FIGS. 8A and 8B shows one embodiment of a PEMF blanket system for use outside the enclosure, however, in certain embodiments it's possible to retrofit a steam device to also include the PEMF blankets. In FIG. 8A, a basic PEMF 200 matt is depicted that includes a bottom mat 202, a short chord 204 or an alternative long chord 208, and a top mat 206. One or both of the bottom mat 202 and top mat 206 can include the one or more PEMF generating coils. In certain embodiments, the bottom mat 202 and top mat 206 can include 1, 2, 3, 4, 5, 6, 7, 8, 19, 10, 15, 20, 30, 40, or 50 coils, depending on the zone of PEMF energy generated. When using both the bottom mat 202 and top mat 206, the pair of coils amplify at a zone of overlap, providing greater definition at the location into which the energy is directed (e.g., closer to a surface of the body, deeper beneath the skin, located equidistant from the front and back of a subject or patient, and in some embodiments, the field can be fluctuated such that the zone or overlap or amplification can be moved around within the body during a treatment. As such, the zone can be moved from a superior to an inferior location, dorsal or ventral, medial or lateral, superficial or deep, ipsilateral or contralateral, in one or more locations at the same time, at different times, in parallel or in series.

FIG. 8B shows one embodiment of a PEMF control unit 210 for use with the present invention. An on/off switch 212 is connected to power supply 214, which control power to the PEMF unit controlled by start/pause button 216, and may also include a reset button 218. This PEMF control unit 210 is depicted with a timer 220, but other display formats may also be used, e.g., a detailed body contour may that shows the amount of energy delivered during a treatment, a display that shows the amount of energy delivered, etc. A fan 222 helps cool the PEMF control unit 210, and in this embodiment a know 224. Finally, the show or long probe cords 228 are connected to the unit, in this embodiment, each of the top and bottom mat 202, 206 are connected to a separate outlet.

Figure 9:
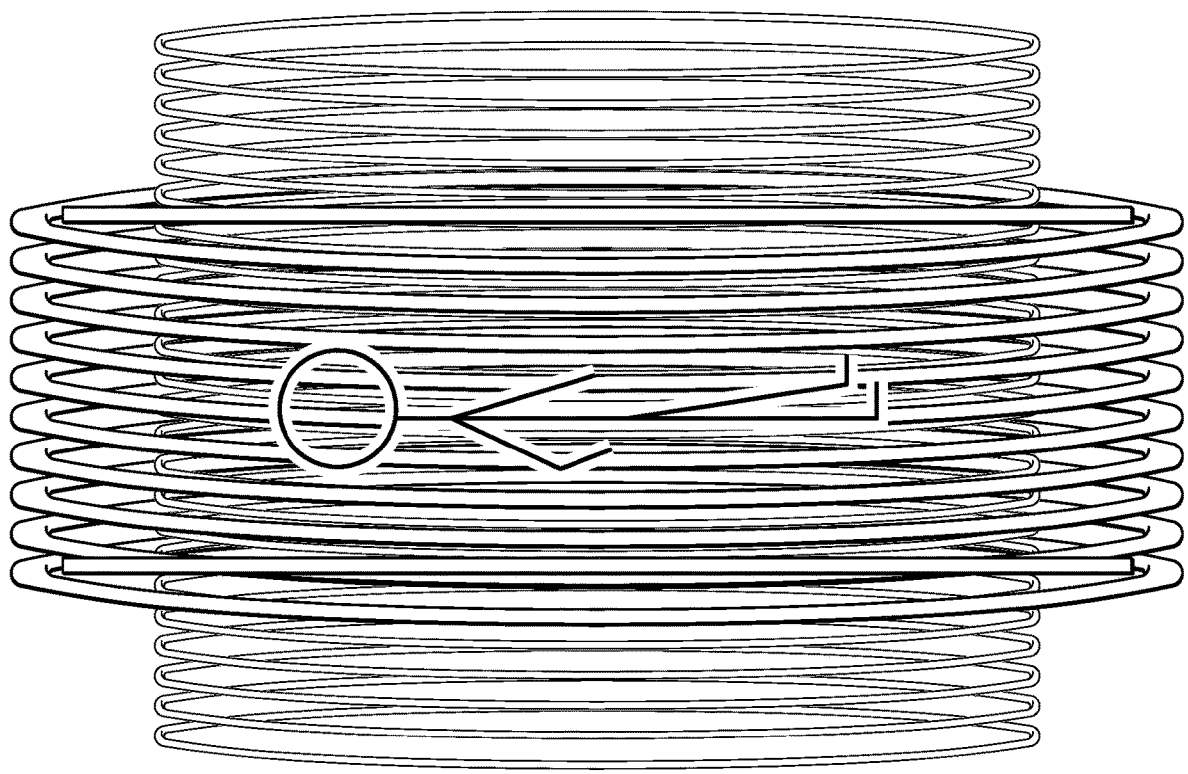
FIG. 9 shows a depiction of the overlap formed by the bottom and top PEMF mats during a treatment session, depicting a single coil.

FIG. 9 shows a depiction of the overlap formed by the bottom and top PEMF mats during a treatment session, depicting a single coil. The skilled artisan will recognize that by including a plurality of coils in the mats (or embedded in the enclosure) a multiplicity of locations can be targeted with the PEMF pulses or treatments of the present invention.

FIG. 10 shows another embodiment of a multimodal treatment device of the present invention that include a screen for the user and a separate unit for enhancing the one or more modalities.

In operation, the PEMF unit helps, among other treatments, to move fluid around the body and enhance cellular metabolism and detoxification, giving your body "cellular exercise". Drinking water helps your body to flush out toxins that are released from the cells. Detoxing the body too fast, especially if there are many toxins present, can overload the body's avenues of elimination (kidneys, liver, colon, lymph system, skin and lungs). Overloading these organs may result in an extreme detox or "herxheimer" reaction. Ultimately a detox reaction is a sign of a good thing (the body trying to eliminate toxins in any way it can). Detoxification is much easier when you support your body's normal elimination systems. When these organs are working well, and there is sufficient water and nutrient intake, then most detox reactions pass quickly, and sometimes even go unnoticed.

Intensity: The intensity of the PEMF that you experience does not only depend on the intensity setting on the front panel of the driver. It also depends on the distance of the mat or accessory from the body, the size of the loops in each coil, the number of loops in a coil, and whether a single mat or accessory mat are over an area, or two mats/accessories simultaneously over the area, etc. A typical course of treatment is from 5 seconds to 12 minutes, however, the time of treatment may be varied depending on the needs of the subject.

Bottom Mat: In certain embodiments, the bottom mat can be inflatable. If the mat includes an inflatable bladder, the bottom mat is inflated manually or automatically with a built-in air fan or pump.

Top mat: Generally, it is not indicated to place the top matt over a subject's head, however, certain limited (but important) modalities of PEMF treatment may include a treatment of the head. Typically, the top mat is only placed to cover the shoulders and down toward the feet. A separate head-only PEMF device may also be used with the present invention.

The PEMF treatment can be varied with the mats or one or more accessories that are especially useful in targeting the extremities (hand and foot areas). The care provider can choose to use one or two of the accessories to target specific areas without doing a full body session with the mats. The care provider may also want to target the gut, kidney and liver area for a few minutes. Alternatively, various muscle groups, limbs or other areas may also be targeted.

In several non-limiting examples of the uses for the present invention, the PEMF treatment may include the following treatments. The skilled artisan will recognize that these treatments can be used alone or in any combination.

Recommended Duration:

3 minutes per area; no more than 12 minutes per session (i.e. max 4 areas per session).

Example 1

Foot (3 mins), Heel (3 mins), Ankle (3 mins), Lower Calf (3 mins)=Total 12 mins.

Example 2

Left Shoulder (3 mins), Right Shoulder (3 mins)=Total 6 mins.

Example 3

Abdominal Area (3 mins)=Total 3 mins.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. An apparatus for transdermal treatments comprising:
a substantially whole-body enclosure for a human subject; and
at least one source for each of three or more treatment modalities, each at least one source for each of the three or more treatment modalities being in communication with the enclosure and consisting of:
at least one source of pulsed electromagnetic fields (PEMF);
at least one source of steam; and
at least one additional source of a treatment modality, wherein the at least one additional source is selected from a group consisting of:
at least one source of ozone;
at least one source of $CO_2$/carbonic acid; and
at least one source of far infrared;
at least one source of pure oxygen;
at least one source of colored light;
at least one source of an essential oil infusion for aromatherapy; and
at least one source of frequency-specific microcurrents.

2. The apparatus of claim 1, wherein the enclosure is a whole-body enclosure with an opening for a head of the human subject.

3. The apparatus of claim 1, wherein the at least one source of the PEMF comprises a plurality of coils sufficient to provide treatment to at least a portion of a body of the human subject, or a whole body of the human subject, concurrently.

4. The apparatus of claim 1, further comprising one or more processors connected to the at least one source for each of the three or more treatment modalities, wherein the one or more processors control one or more valves that open or close an introduction of treatment modalities into the enclosure, or wherein the at least one source of PEMF is controlled separately.

5. The apparatus of claim 1, wherein the at least one source for ozone comprises an ozone sauna, topical cupping, or both.

6. The apparatus of claim 1, wherein the enclosure is adapted to include an article of exercise equipment.

7. The apparatus of claim 1, wherein the at least one source for ozone comprises an ozone vaginal insufflation probe; ozone generators; an auxiliary ozone feed for simultaneous vaginal insufflation and cupping with or without an ozone sauna; or an ozone water drinking source; or combinations thereof.

8. The apparatus of claim 1, wherein the at least one source of the frequency-specific microcurrents has at least one source for one or more specific, programmable frequency-specific microcurrents.

9. The apparatus of claim 1, wherein the at least one source for each of the three or more treatment modalities is provided concurrently, in series, during overlapping time periods, continuously, in a pulsatile manner, or in combinations thereof.

10. The apparatus of claim 1, further comprises a processor, wherein the three or more treatment modalities are programmed into the processor to optimize treatment of the human subject.

11. The apparatus of claim 1, further comprising a heart rate monitor that performs at least one operation selected from: tracking a heart rate, turning off the apparatus when a certain combination of heart rate and time is reached, and performing an emergency shutdown.

12. The apparatus of claim 1, further comprising an ozone degradator that degrades the ozone into $O_2$ prior to exiting the enclosure.

13. The apparatus of claim 1, wherein the at least one source for the PEMF has at least one source for two overlapping fields formed within the enclosure to provide the human subject with at least partially amplified magnetic fields.

14. The apparatus of claim 1, wherein the at least one source of pulsed electromagnetic fields (PEMF) comprises two pads capable of being positioned on opposite sides of the human subject.

15. A method of transdermal treatment of a human subject comprising:
providing an apparatus for transdermal treatment of the human subject comprising:
an enclosure that substantially covers a body of the human subject; and
at least one source for each of three or more treatment modalities, each at least one source for each of the three or more treatment modalities being in communication with the enclosure and consisting of:
at least one source of pulsed electromagnetic fields (PEMF);
at least one source of steam; and
at least one additional source of a treatment modality, wherein the at least one additional source is selected from a group consisting of:
at least one source of ozone;
at least one source of $CO_2$/carbonic acid; and
at least one source of far infrared;
at least one source of pure oxygen;
at least one source of colored light;
at least one source of an essential oil infusion for aromatherapy; and
at least one source of frequency-specific microcurrents.

16. The method of claim 15, further comprising the steps of providing a session to the human subject that comprises: a $CO_2$/carbonic acid treatment for 0 to 8 minutes, an ozone cycle of 0 to 25 minutes, a high intensity PEMF for 0 to 12 minutes, and a sauna or a far infrared treatment, or both; or an ozone cycle of up to 30 minutes if $CO_2$ is set to 0 minutes.

17. The method of claim 15, further comprising the steps of providing a session to the human subject that comprises: a $CO_2$/carbonic acid treatment from 3 to 8 minutes concurrently with an ozone cycle of 0 to 25 minutes, and a high intensity PEMF of 0 to 12 minutes, and a sauna or a far infrared treatment, or both.

18. The method of claim 15, wherein the enclosure is a whole-body enclosure with an opening for a head of the human subject.

19. The method of claim 15, wherein the at least one source of the PEMF comprises one or more coils sufficient to provide treatment to at least a portion of a body of the human subject, or a whole body of the human subject, concurrently.

20. The method of claim 15, further comprising controlling one or more valves that open or close an introduction of treatment modalities into the enclosure, or the at least one source of the PEMF separately.

21. The method of claim 15, wherein the at least one source of the ozone comprises an ozone sauna, topical cupping, or both.

22. The method of claim 15, wherein the enclosure is adapted to include an article of exercise equipment.

23. The method of claim 15, wherein the at least one source for ozone has an ozone vaginal insufflation probe; two ozone generators; an auxiliary ozone feed for simultaneous vaginal insufflation and cupping with or without an ozone sauna; or an ozone water drinking source; or combinations thereof.

24. The method of claim 15, wherein the at least one source of the frequency-specific microcurrents has at least one source for one or more specific, programmable frequency-specific microcurrents.

25. The method of claim 15, wherein the at least one source for each of the three or more treatment modalities is provided concurrently, in series, during overlapping time periods, continuously, in a pulsatile manner, or in combinations thereof.

26. The method of claim 15, wherein the apparatus for transdermal treatment of the human subject has a heart rate monitor that performs at least one operation selected from: tracking a heart rate, turning off the apparatus when a certain combination of heart rate and time is reached, and performing an emergency shutdown.

27. The method of claim 15, wherein the apparatus for transdermal treatment of the human subject further has an ozone degradator that degrades the ozone into $O_2$ prior to exiting the enclosure.

28. The method of claim 15, further comprising identifying a transdermal treatment for the subject and controlling a type of treatment modality and a time to treat the subject.

29. The method of claim 15, wherein the at least one source for the PEMF comprises at least one source for two overlapping fields formed within the enclosure to provide the human subject with at least partially amplified magnetic fields.

30. The method of claim 15, wherein the at least one source of pulsed electromagnetic fields (PEMF) comprises two pads capable of being positioned on opposite sides of the human subject.

31. An apparatus for transdermal treatments of a human subject comprising:
   a whole-body enclosure for the human subject; and
   at least one source for each of three or more treatment modalities, each at least one source for each of the three or more treatment modalities being in communication with the enclosure and consisting of:
      at least one source of pulsed electromagnetic fields (PEMF);
      at least one source of steam; and
      at least one additional source of a treatment modality, wherein the at least one additional source is selected from a group consisting of:
      at least one source of ozone;
      at least one source of $CO_2$/carbonic acid;
      at least one source of far infrared;
      at least one source of pure oxygen;
      at least one source of colored light;
      at least one source of an essential oil infusion for aromatherapy; and
      at least one source of frequency-specific microcurrents;
   wherein the three or more treatment modalities detoxify a body of the human subject, improves circulation, boosts energy, strengthens an immune system, or some combination.

32. The apparatus of claim 31, wherein the at least one source of pulsed electromagnetic fields (PEMF) comprises:
   two pads capable of being positioned on opposite sides of the human subject.

* * * * *